(12) United States Patent
Ohashi et al.

(10) Patent No.: US 12,064,275 B2
(45) Date of Patent: Aug. 20, 2024

(54) X-RAY DIAGNOSTIC APPARATUS

(71) Applicant: CANON MEDICAL SYSTEMS CORPORATION, Otawara (JP)

(72) Inventors: Shumpei Ohashi, Otawara (JP); Hisato Takemoto, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 244 days.

(21) Appl. No.: 17/643,480

(22) Filed: Dec. 9, 2021

(65) Prior Publication Data

US 2022/0183640 A1 Jun. 16, 2022

(30) Foreign Application Priority Data

Dec. 10, 2020 (JP) .................................. 2020-205233

(51) Int. Cl.
*A61B 6/00* (2024.01)
*A61B 6/06* (2006.01)
*A61B 6/42* (2024.01)

(52) U.S. Cl.
CPC .............. *A61B 6/4441* (2013.01); *A61B 6/06* (2013.01); *A61B 6/4208* (2013.01); *A61B 6/4291* (2013.01); *A61B 6/5282* (2013.01); *A61B 6/54* (2013.01)

(58) Field of Classification Search
CPC ....... A61B 6/06; A61B 6/4208; A61B 6/4291; A61B 6/4441; A61B 6/4452; A61B 6/5282; A61B 6/54; A61B 6/588
See application file for complete search history.

(56) References Cited

U.S. PATENT DOCUMENTS

| 5,930,328 | A | * | 7/1999 | Nakamura | A61B 6/547 378/115 |
| 6,412,978 | B1 | * | 7/2002 | Watanabe | A61B 6/4441 378/197 |
| 7,748,899 | B2 | * | 7/2010 | Saladin | A61B 6/4441 378/197 |
| 9,105,366 | B2 | * | 8/2015 | Hruschka | G21K 1/025 |
| 2002/0122532 | A1 | * | 9/2002 | Mioitti | A61B 6/4291 378/154 |
| 2005/0089143 | A1 | * | 4/2005 | Nakano | A61B 6/504 378/98.12 |
| 2006/0039537 | A1 | * | 2/2006 | Strobel | G06T 11/005 378/197 |

(Continued)

FOREIGN PATENT DOCUMENTS

JP 2017-153591 A 9/2017

*Primary Examiner* — Dani Fox
*Assistant Examiner* — Soorena Kefayati
(74) *Attorney, Agent, or Firm* — Oblon, McClelland, Maier & Neustadt, L.L.P.

(57) ABSTRACT

An X-ray diagnostic apparatus according to an embodiment includes an X-ray detector, a grid, a slide mechanism, a rotary mechanism, and an arm. The X-ray detector detects X-rays emitted from an X-ray tube. The grid has a fixed relative position to the X-ray detector and is provided with stripes extending in a first direction to remove scattered rays included in the X-rays. The slide mechanism includes at least one slide rail along the first direction and holds the X-ray detector so as to slide in the first direction. The rotary mechanism includes a rotation shaft and rotatably holds the slide mechanism. The arm holds the rotary mechanism and is operable.

10 Claims, 10 Drawing Sheets

(56) References Cited

U.S. PATENT DOCUMENTS

| | | | |
|---|---|---|---|
| 2006/0182225 A1* | 8/2006 | Besson | A61B 6/06 378/146 |
| 2006/0198497 A1* | 9/2006 | Gotoh | A61B 6/588 378/197 |
| 2006/0215817 A1* | 9/2006 | Watanabe | A61B 6/4441 378/114 |
| 2006/0222148 A1* | 10/2006 | Boese | G03B 42/02 378/179 |
| 2010/0239145 A1* | 9/2010 | Fujita | A61B 6/4441 378/62 |
| 2010/0303202 A1* | 12/2010 | Ren | A61B 6/502 378/62 |
| 2011/0013742 A1* | 1/2011 | Zaiki | A61B 6/06 378/15 |
| 2011/0096894 A1* | 4/2011 | Uehara | A61B 6/4233 378/19 |
| 2011/0110500 A1* | 5/2011 | Fujita | A61B 6/5282 378/154 |
| 2011/0188624 A1* | 8/2011 | Ren | A61B 6/06 378/150 |
| 2011/0200169 A1* | 8/2011 | Oikawa | A61B 6/4452 378/42 |
| 2011/0317811 A1* | 12/2011 | Scarpellini | A61B 6/4476 378/62 |
| 2012/0257725 A1* | 10/2012 | Noda | A61B 6/4233 378/197 |
| 2012/0275570 A1* | 11/2012 | Li | A61B 6/583 378/155 |
| 2015/0085990 A1* | 3/2015 | Virshup | A61B 6/4283 378/154 |
| 2015/0208996 A1* | 7/2015 | Kyriakou | G06T 7/11 600/431 |
| 2016/0206262 A1* | 7/2016 | Langan | A61B 6/4441 |
| 2016/0228080 A1* | 8/2016 | Margot | A61B 6/4441 |
| 2017/0112456 A1* | 4/2017 | Ohga | A61B 6/487 |
| 2017/0135651 A1* | 5/2017 | Kugler | A61B 6/482 |
| 2017/0245826 A1* | 8/2017 | Kasaoka | A61B 6/4452 |
| 2018/0199901 A1* | 7/2018 | Schraven | A61B 6/0487 |
| 2018/0271464 A1* | 9/2018 | Abe | A61B 6/463 |
| 2020/0054297 A1* | 2/2020 | Martinez Ferreira | A61B 6/4441 |
| 2020/0085399 A1* | 3/2020 | Okutani | A61B 6/588 |
| 2021/0007700 A1* | 1/2021 | Withagen | A61B 6/4441 |
| 2021/0059621 A1* | 3/2021 | Okutani | A61B 6/588 |
| 2021/0236069 A1* | 8/2021 | Kotian | A61B 6/102 |
| 2021/0259653 A1* | 8/2021 | Yesudhas | A61B 6/4452 |

* cited by examiner

X-RAY DIAGNOSTIC APPARATUS

CROSS-REFERENCE TO RELATED APPLICATIONS

This application is based upon and claims the benefit of priority from Japanese Patent Application No. 2020-205233, filed on Dec. 10, 2020; the entire contents of which are incorporated herein by reference.

FIELD

Embodiments described herein relate generally to an X-ray diagnostic apparatus.

BACKGROUND

There are conventionally known X-ray diagnostic apparatuses, such as X-ray angiography devices, capable of changing the position of an X-ray detector by operating an arm. For such an X-ray diagnostic apparatus, there is a demand for a large-sized X-ray detector having a size of, for example, 12 inches per side in order to increase the imaging field of view. When the X-ray detector has a large size, however, the X-ray detector is likely to interfere with the subject, and the movement of the arm during imaging may be limited.

DETAILED DESCRIPTION

Embodiments of an X-ray diagnostic apparatus are described below in detail with reference to the drawings.

First Embodiment

An X-ray diagnostic apparatus according to an embodiment includes an X-ray detector, a grid, a slide mechanism, a rotary mechanism, and an arm. The X-ray detector detects X-rays emitted from an X-ray tube. The grid has a fixed relative position to the X-ray detector and is provided with stripes extending in a first direction to remove scattered rays included in the X-rays. The slide mechanism includes at least one slide rail along the first direction and holds the X-ray detector so as to slide in the first direction. The rotary mechanism includes a rotation shaft and rotatably holds the slide mechanism. The arm holds the rotary mechanism and is operable.

Figure 1:
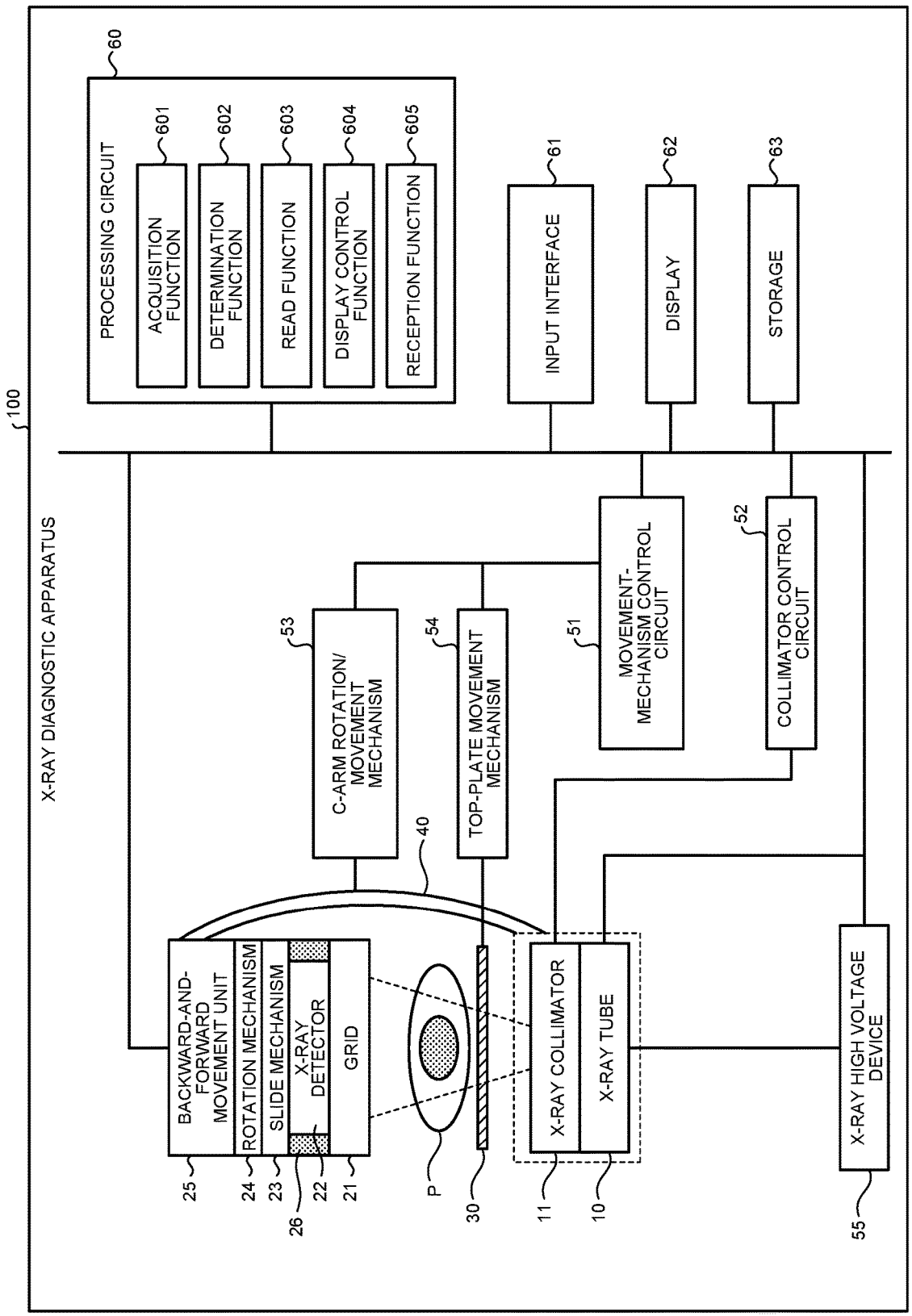
FIG. 1 is a block diagram illustrating an example of a configuration of an X-ray diagnostic apparatus according to a first embodiment.

FIG. 1 is a block diagram illustrating an example of the configuration of an X-ray diagnostic apparatus 100 according to a first embodiment. As illustrated in FIG. 1, the X-ray diagnostic apparatus 100 includes an X-ray tube 10, an X-ray collimator 11, a grid 21, an X-ray detector 22, a slide mechanism 23, a rotation mechanism 24, a backward-and-forward movement unit 25, a sensor 26, a top plate 30, a C arm 40, a movement-mechanism control circuit 51, a collimator control circuit 52, a C-arm rotation/movement mechanism 53, a top-plate movement mechanism 54, an X-ray high voltage device 55, a processing circuit 60, an input interface 61, a display 62, and storage 63.

The X-ray diagnostic apparatus 100 according to the present embodiment is, for example, an X-ray angiography apparatus.

The top plate 30 is a bed where a subject P is placed and is provided on a bed device (not illustrated). The subject P is, for example, a patient and is not included in the X-ray diagnostic apparatus 100.

The top-plate movement mechanism 54 is a mechanism that moves and tilts the top plate 30. For example, the top-plate movement mechanism 54 moves and tilts the top plate 30 by using the power generated by an actuator under the control of the movement-mechanism control circuit 51. For example, it is assumed that the top plate 30 may be moved and tilted in a horizontal direction (longitudinal direction) or an up-down direction (vertical direction).

The collimator control circuit 52 adjusts the aperture of collimator blades included in the X-ray collimator 11 to control the irradiation range of X-rays with which the subject P is irradiated under the control of the processing circuit 60. A configuration of the X-ray collimator 11 is described below.

The X-ray high voltage device 55 is a high voltage power source that generates a high voltage and supplies the generated high voltage to the X-ray tube 10 under the control of the processing circuit 60.

The C arm 40 holds the rotation mechanism 24 and is operable. More specifically, the C arm 40 holds the X-ray tube 10, the X-ray collimator 11, the grid 21, the X-ray detector 22, the slide mechanism 23, the rotation mechanism 24, the backward-and-forward movement unit 25, and the sensor 26. The C arm 40 is moved in upward, downward, leftward, and rightward directions or is rotationally moved by the C-arm rotation/movement mechanism 53. The C arm 40 is an example of an arm according to the present embodiment.

The C-arm rotation/movement mechanism 53 is a drive mechanism that moves the C arm 40 and includes a motor, an actuator, and the like. The C-arm rotation/movement mechanism 53 moves the C arm 40 in the upward, downward, leftward, and rightward directions or rotationally moves the C arm 40 under the control of the movement-mechanism control circuit 51.

Figure 2:
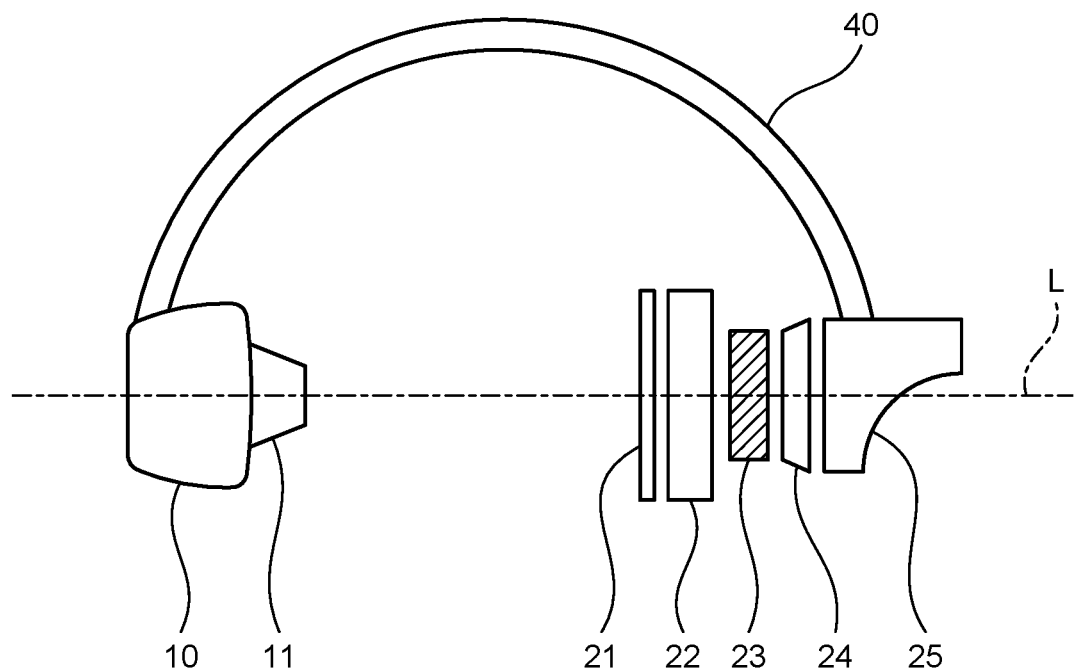
FIG. 2 is a diagram illustrating an example of a configuration of a C arm according to the first embodiment.

FIG. 2 is a diagram illustrating an example of the configuration of the C arm 40 according to the first embodiment.

As illustrated in FIGS. 1 and 2, the X-ray tube 10 and the X-ray collimator 11 are provided at one of the two opposing ends of the C arm 40. At the other end, the grid 21, the X-ray detector 22, the slide mechanism 23, the rotation mechanism 24, and the backward-and-forward movement unit 25 are provided. The sensor 26 is not illustrated in FIG. 2.

The grid 21, the X-ray detector 22, the slide mechanism 23, and the rotation mechanism 24 are provided at the backward-and-forward movement unit 25 included in the C arm 40 so as to move backward and forward. The grid 21, the X-ray detector 22, and the slide mechanism 23 are provided at the rotation mechanism 24 so as to move backward and forward. The grid 21 and the X-ray detector 22 are provided at the slide mechanism 23 so as to slide. In the initial position, the X-ray tube 10, the X-ray collimator 11, the grid 21, the X-ray detector 22, the slide mechanism 23, and the rotation mechanism 24 are provided such that, for example, the center of each component is located at a straight line L as illustrated in FIG. 2.

The individual components included in the C arm 40 are described below.

The X-ray tube 10 is a vacuum tube including a cathode (filament) that generates thermoelectrons and an anode (target) that generates X-rays upon collision of thermoelectrons. The X-ray tube 10 uses the high voltage supplied from the X-ray high voltage device 55 to emit thermoelectrons from the cathode toward the anode so as to generate X-rays. The X-ray tube 10 is also referred to as an X-ray tube bulb.

The X-ray collimator 11 narrows the X-rays emitted from the X-ray tube 10. For example, the X-ray collimator 11 includes a plurality of collimator blades made of a metal plate such as lead. The collimator blades are driven by a collimator-blade drive device (not illustrated) in accordance with the region of interest under the control of the collimator control circuit 52. The X-ray collimator 11 slides the collimator blades by the collimator-blade drive device to adjust the X-ray shielding region to any size.

The X-ray detector 22 detects X-rays emitted from the X-ray tube 10. The X-ray detector 22 is, for example, an X-ray planar detector (flat panel detector: FPD) including detection elements arranged in a matrix. According to the present embodiment, for example, the X-ray detector 22 has a size of 12 inches or more per side. The size is an example, and the size of the X-ray detector 22 is not limited thereto. The X-ray detector 22 detects the X-rays emitted from the X-ray tube 10 and transmitted through the subject P and outputs a detection signal corresponding to the detected X-ray dose to the processing circuit 60.

The slide mechanism 23 holds the X-ray detector 22 so as to slide in the first direction. The first direction is a direction along a stripe on the grid 21. The stripe is a striped pattern corresponding to the gap between metal plates, and the direction along the stripe refers to the longitudinal direction of the metal plate (lead foil, etc.) of the grid 21. The first direction is also referred to as a slide axis direction of the slide mechanism 23.

According to the present embodiment, the slide mechanism 23 slides the X-ray detector 22 along the first direction in accordance with the slide amount determined by the movement-mechanism control circuit 51. The slide mechanism 23 includes, for example, a board, a rail that is fixed onto the board, a motor, and an actuator and slides the X-ray detector 22 on the rail under the control of the movement-mechanism control circuit 51. The relative position between the grid 21 and the X-ray detector 22 is fixed, and therefore when the slide mechanism 23 slides the X-ray detector 22, the grid 21 is also slid together with the X-ray detector 22.

Figure 3:
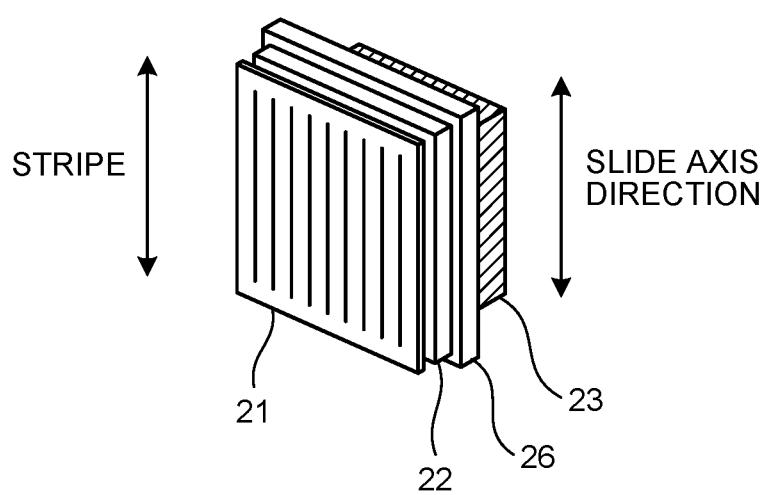
FIG. 3 is a diagram illustrating a stripe of a grid and a slide axis direction of a slide mechanism according to the first embodiment.

FIG. 3 is a diagram illustrating the stripe on the grid 21 and the slide axis direction of the slide mechanism 23 according to the first embodiment.

The grid 21 removes scattered ray components of the X-rays having transmitted through the subject P. The grid 21 has a fixed relative position to the X-ray detector 22 and is provided with stripes extending in the first direction.

More specifically, the grid 21 is a parallel grid that is configured by, for example, arranging a plurality of metal plates (lead foil, etc.), which absorbs X-rays, in parallel along the first direction with a gap formed therebetween.

Even when the grid 21 and the X-ray detector 22 are slid along the first direction in parallel to the stripe, the X-ray irradiation angle with respect to the stripe on the grid 21 does not change, and thus the function to remove scattered ray components may be maintained.

The grid 21 is not limited to a parallel grid. For example, the grid 21 may be a focused grid in which a plurality of metal plates is arranged to tilt toward an X-ray focal point. The grid 21 may be filled with an intermediate substance having low X-ray absorption, instead of forming a gap between the metal plates. Specifically, the grid 21 may be configured by alternately arranging a metal plate that absorbs X-rays and an intermediate substance that absorbs less X-rays.

The rotation mechanism 24 rotatably holds the slide mechanism 23. The rotation mechanism 24 includes, for example, a rotation shaft, a motor, and an actuator and rotates the slide mechanism 23 by rotating the board of the slide mechanism 23 under the control of the movement-mechanism control circuit 51. The rotation mechanism 24 rotates the slide mechanism 23 in accordance with the rotation angle determined by the movement-mechanism control circuit 51.

Figure 4:
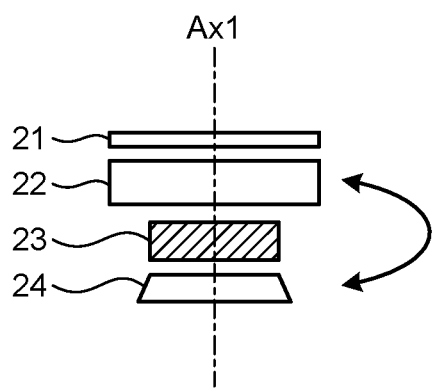
FIG. 4 is a diagram illustrating a rotation mechanism according to the first embodiment.

FIG. 4 is a diagram illustrating the rotation mechanism 24 according to the first embodiment. As illustrated in FIG. 4, the rotation mechanism 24 is rotatable about a rotation axis Ax1. The rotation axis Ax1 is, for example, a line connecting the center of the rotation mechanism 24 and the X-ray tube 10.

When the rotation mechanism 24 rotates the slide mechanism 23, the grid 21 and the X-ray detector 22 also rotate together with the slide mechanism 23.

The backward-and-forward movement unit 25 adjusts a source-to-image receptor distance (source image distance: SID), which is the distance between the X-ray tube 10 and the X-ray detector 22. More specifically, the backward-and-forward movement unit 25 moves the rotation mechanism 24 in a direction close to or away from the X-ray tube 10 under the control of the movement-mechanism control circuit 51. For example, the backward-and-forward movement unit 25 rotates a ball screw by an actuator to adjusts the SID.

When the backward-and-forward movement unit 25 moves the rotation mechanism 24, the grid 21, the X-ray detector 22, and the slide mechanism 23 also move together with the rotation mechanism 24. According to the present embodiment, the movement of the X-ray detector 22 in a direction close to the X-ray tube 10 is referred to as a forward movement, and the movement of the X-ray detector 22 in a direction away from the X-ray tube 10 is referred to as a backward movement. The moving direction and the moving amount are determined by the movement-mechanism control circuit 51. The backward-and-forward movement unit 25 is an example of a backward-and-forward movement mechanism according to the present embodiment.

When the X-ray detector 22 and the subject P approach each other by a specified distance or less, the sensor 26 detects the approach. When it is detected that the X-ray detector 22 and the subject P have approached each other by the specified distance or less, the sensor 26 sends the detection result to the movement-mechanism control circuit 51. The sensor 26 is an example of a detection unit according to the present embodiment.

The specified distance is not particularly limited, but may be about several centimeters or may be zero, i.e., may be the state where the subject P and the X-ray detector 22 are in contact with each other. In other words, the sensor 26 may detect the contact between the X-ray detector 22 and the subject P in advance or may detect the actual contact. The sensor 26 may be, for example, a capacitive sensor or a contact sensor. Alternatively, the sensor 26 may detect the approach by using an optical method such as a camera. The detection result by the sensor 26 may indicate, for example, only the presence or absence of approach between the X-ray detector 22 and the subject P or may indicate the distance between the X-ray detector 22 and the subject P.

Figure 5:
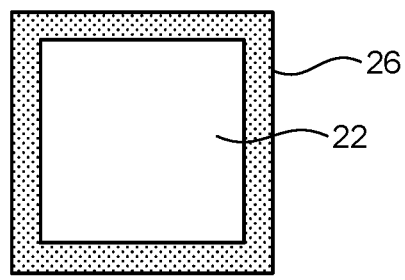
FIG. 5 is a diagram illustrating an example of an installation position of a sensor according to the first embodiment.

FIG. 5 is a diagram illustrating an example of an installation position of the sensor 26 according to the first embodiment. As illustrated in FIG. 5, the sensor 26 is provided to surround the X-ray detector 22, for example.

The sensor 26 may detect not only the approach between the X-ray detector 22 and the subject P but also the approach between the X-ray detector 22 and an object such as the top plate 30. The object to be detected is not limited to a component inside the X-ray diagnostic apparatus 100, but may be another apparatus or the like around the X-ray diagnostic apparatus 100.

With reference back to FIG. 1, the movement-mechanism control circuit 51 controls the slide mechanism 23, the rotation mechanism 24, the backward-and-forward movement unit 25, the C-arm rotation/movement mechanism 53, and the top-plate movement mechanism 54.

For example, the movement-mechanism control circuit 51 determines the slide amount of the X-ray detector 22 based on the angle of the C arm 40 and sends the determined slide amount to the slide mechanism 23. The slide mechanism 23 slides the X-ray detector 22 by the slide amount determined by the movement-mechanism control circuit 51 to control the slide amount of the X-ray detector 22 based on the angle of the C arm 40.

The slide amount according to the present embodiment includes the sliding direction and the sliding distance.

Figure 6:
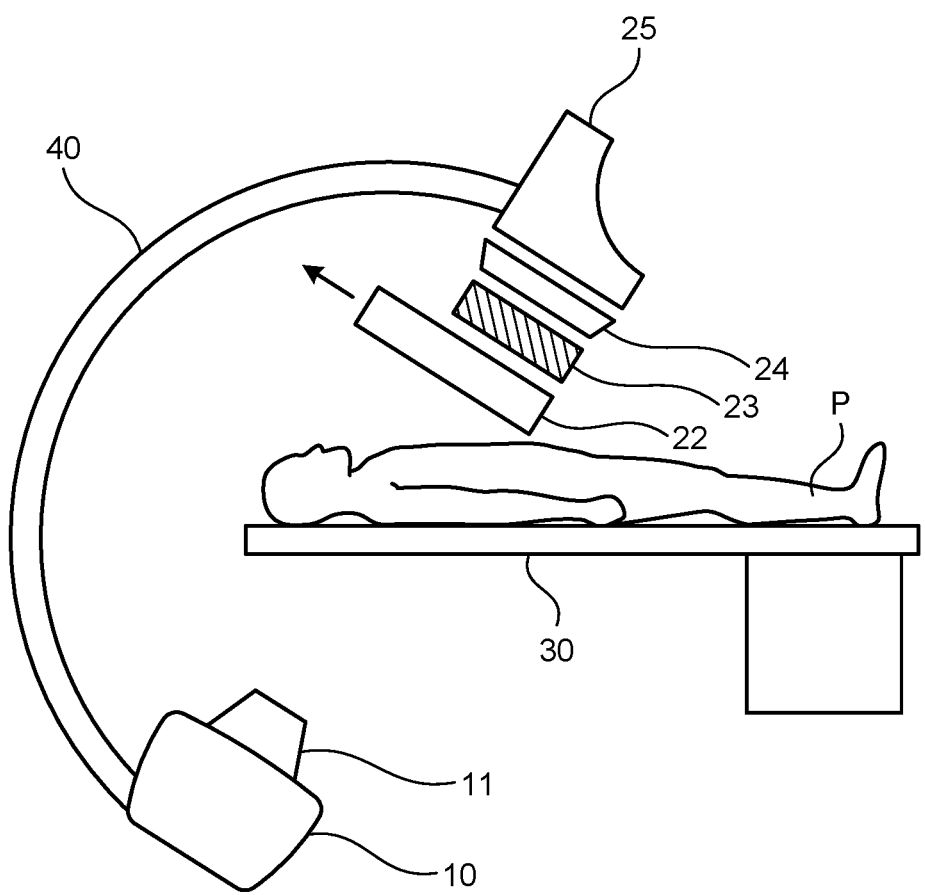
FIG. 6 is a diagram illustrating an example of sliding of an X-ray detector according to the first embodiment.

FIG. 6 is a diagram illustrating an example of sliding of the X-ray detector 22 according to the first embodiment. The grid 21 is not illustrated in FIG. 6. In the example illustrated in FIG. 6, the C arm 40 is largely tilted toward the head of the subject P such that the heart of the subject P falls within the irradiation range of X-rays. When the C arm 40 is tilted in this way, the X-ray detector 22 approaches the chest and abdomen of the subject P. Therefore, in the example illustrated in FIG. 6, the slide mechanism 23 slides the X-ray detector 22 in a direction away from the subject P with respect to the initial position. If the X-ray detector 22 remains in the initial position at the angle of the C arm 40 illustrated in FIG. 6, the X-ray detector 22 comes into contact with the subject P, which makes imaging difficult. As the X-ray detector 22 is slidable, imaging is facilitated with the C arm 40 largely tilted.

In some positional relationship between the C arm 40 and the top plate 30, there may be a mismatch between the direction in which the X-ray detector 22 moves away from the subject P, i.e., the direction in which the X-ray detector 22 is to slide, and the operating axis of the slide mechanism 23, i.e., the first direction. In such a case, the rotation mechanism 24 rotates the slide mechanism 23 such that the first direction becomes parallel to the direction away from the subject P based on the operating direction of the C arm 40 and the position of the top plate 30.

For example, the movement-mechanism control circuit 51 may determine the direction in which the X-ray detector 22 approaches the top plate 30 or the subject P based on the operating direction of the C arm 40 and determine the direction in which the X-ray detector 22 moves away from the subject P and the first direction. In this case, the movement-mechanism control circuit 51 determines the rotation angle such that the direction in which the X-ray detector 22 moves away from the subject P matches the first direction and sends the determined rotation angle to the rotation mechanism 24. The rotation mechanism 24 rotates the slide mechanism 23 by the rotation angle determined by the movement-mechanism control circuit 51.

As the position of the X-ray detector 22 with respect to the subject P changes in accordance with the imaging field of view (FOV), the movement-mechanism control circuit 51 may acquire the setting information on the FOV from, for example, the processing circuit 60 and determine the slide amount of the X-ray detector 22 based on the FOV and the angle of the C arm 40. The slide mechanism 23 slides the X-ray detector 22 by the slide amount determined by the movement-mechanism control circuit 51 to control the slide amount of the X-ray detector 22 based on the FOV and the angle of the C arm 40.

The position of the X-ray detector 22 suitable for imaging changes in accordance with not only the angle of the C arm 40 but also the relative positional relationship between the C arm 40 and the subject P on the top plate 30. For example, even when the angle of the C arm 40 is identical, the distance between the X-ray detector 22 and the subject P changes due to a difference in the position of the top plate 30. Therefore, the movement-mechanism control circuit 51 according to the present embodiment determines the slide amount of the X-ray detector 22 based on the angle of the C arm 40 and the position of the top plate 30 to avoid the contact between the X-ray detector 22 and the subject P with high accuracy. The slide mechanism 23 slides the X-ray detector 22 by the slide amount determined by the movement-mechanism control circuit 51 to control the slide amount of the X-ray detector 22 based on the angle of the C arm 40 and the position of the top plate 30. According to the present embodiment, the position of the top plate 30 includes the tilt angle of the top plate 30.

Figure 7:
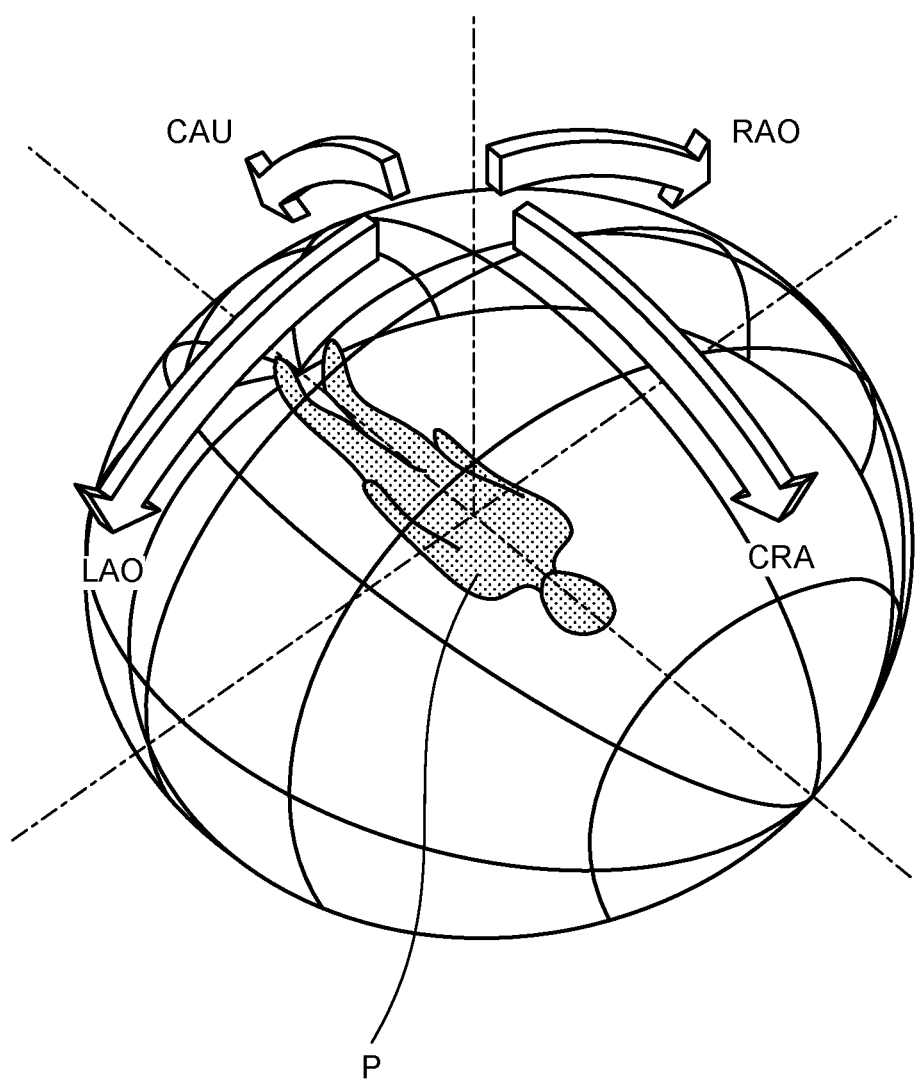
FIG. 7 is a diagram illustrating a clinical angle for a subject according to the first embodiment.

Here, the tilt of the C arm 40 with respect to the subject P is referred to as a clinical angle. FIG. 7 is a diagram illustrating the clinical angle for the subject P according to the first embodiment. The top plate 30 where the subject P is placed is not illustrated in FIG. 7. As illustrated in FIG. 7, the clinical angle is represented by an angle of the subject P in each direction, i.e., caudal (CAU), cranial (CRA), right anterior oblique (RAO), and left anterior oblique (LAO). In the example described in FIG. 6, the C arm 40 is tilted toward the CRA at a large angle.

Typically, during coronary angiography (CAG) using a catheter or cardiac percutaneous coronary intervention (PCI), the C arm 40 is often tilted to have a large angle of, in particular, CAU or CRA as there is a need to observe the heart of the subject P at multiple angles. When the angle of CAU or CRA is large, the subject P and the X-ray detector 22 are likely to approach each other.

Therefore, the movement-mechanism control circuit 51 according to the present embodiment determines the slide amount of the X-ray detector 22 based on the clinical angle that is calculated based on the angle of the C arm 40 and the position of the top plate 30. The slide mechanism 23 slides the X-ray detector 22 by the slide amount determined by the movement-mechanism control circuit 51 to control the slide amount of the X-ray detector 22 based on the clinical angle. The clinical angle may be calculated by the movement-mechanism control circuit 51 or may be calculated by the processing circuit 60 described below.

The movement-mechanism control circuit 51 determines the limit of the slide amount such that the X-ray irradiation range falls within a detection surface of the X-ray detector 22.

Figure 8:
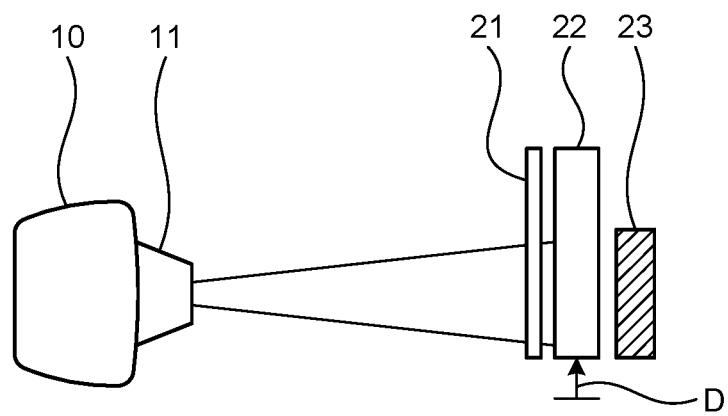
FIG. 8 is a diagram illustrating an upper limit of a slide distance of the X-ray detector according to the first embodiment.

FIG. 8 is a diagram illustrating an upper limit of a slide distance of the X-ray detector 22 according to the first embodiment. In the example illustrated in FIG. 8, the X-ray detector 22 slides by a distance D from the initial position along the first direction. In this state, the lower end of the X-ray detector 22 in FIG. 8 reaches the lower end of the X-ray irradiation range, and therefore the distance D is the upper limit of the slide distance of the X-ray detector 22 in the X-ray irradiation range.

The X-ray irradiation range changes in accordance with the size of the FOV. When the FOV is smaller than that in the example illustrated in FIG. 8, the X-ray irradiation range is also smaller, and therefore the X-ray detector 22 may slide by a distance longer than the distance D.

The longer the distance the X-ray detector 22 may slide, the greater the flexibility in making the angle of the C arm 40. For example, when the size of the X-ray detector 22 per side is 12 inches and the slide distance of the X-ray detector 22 is approximately 5 cm in one direction along the first direction from the initial position and also approximately 5 cm in the other direction, the flexibility in making the angle of the C arm 40 increases to the same extent as that in a case where an X-ray detector having a size of 8 inches per side is used.

More specifically, the movement-mechanism control circuit 51 determines the slide amount of the X-ray detector 22 based on the region corresponding to the FOV on the X-ray detector 22. The movement-mechanism control circuit 51 may acquire the setting information on the FOV from, for example, the processing circuit 60 and determine the position and size of the region corresponding to the FOV on the X-ray detector 22 based on the acquired setting information.

Alternatively, the storage 63 may previously store the setting information on the FOV and the upper limit of the slide distance of the X-ray detector 22 in association with each other. In this case, the movement-mechanism control circuit 51 may acquire the upper limit of the slide distance corresponding to the setting information on the current FOV from the storage 63 and, based on the upper limit, the angle of the C arm 40, and the position of the top plate 30, determine the slide amount of the X-ray detector 22.

That is, the slide mechanism 23 slides the X-ray detector 22 by the slide amount determined by the movement-mechanism control circuit 51 to control the slide amount of the X-ray detector 22 based on the region corresponding to the FOV on the X-ray detector 22.

The movement-mechanism control circuit 51 determines that the direction away from the subject P along the first direction is a sliding direction when the sensor 26 detects the approach between the X-ray detector 22 and the subject P. In this case, the slide mechanism 23 slides the X-ray detector 22 in the sliding direction determined by the movement-mechanism control circuit 51 to slide the X-ray detector 22 in the direction away from the subject P along the first direction.

As described above, as the upper limit of the slide distance is determined based on the region corresponding to the FOV on the X-ray detector 22, the movement-mechanism control circuit 51 determines the slide amount based on the detection result of the approach between the X-ray detector 22 and the subject P by the sensor 26 and the region corresponding to the FOV on the X-ray detector 22. The slide mechanism 23 slides the X-ray detector 22 by the slide amount determined by the movement-mechanism control circuit 51 to slide the X-ray detector 22 based on the detection result of the approach between the X-ray detector 22 and the subject P by the sensor 26 and the region corresponding to the FOV on the X-ray detector 22.

As described above, when there is a mismatch between the direction in which the X-ray detector 22 is to be retracted and the first direction, the X-ray detector 22 needs to be rotated before the X-ray detector 22 is slid. Therefore, for example, the movement-mechanism control circuit 51 may determine the direction in which the X-ray detector 22 approaches the top plate 30 or the subject P based on the operating direction of the C arm 40, and before the sensor 26 detects the approach to the subject P, rotate the X-ray detector 22 by the rotation mechanism 24 such that the direction in which the X-ray detector 22 moves away from the subject P matches the first direction.

Although the detection result of the approach between the X-ray detector 22 and the subject P by the sensor 26 is used according to the present embodiment, the movement-mechanism control circuit 51 may eliminate the use of the detection result by the sensor 26. For example, the storage 63 may previously store a clinical angle at which the distance between the X-ray detector 22 and the subject P may be equal to or less than the specified distance. In this case, the movement-mechanism control circuit 51 may determine the slide amount of the X-ray detector 22 based on the measure of the clinical angle at which the distance between the X-ray detector 22 and the subject P may be less than or equal to the specified distance, the current clinical angle, and the currently set FOV. Alternatively, the movement-mechanism control circuit 51 may use a combination of the determination of the slide amount using the clinical angle at which the distance between the X-ray detector 22 and the subject P may be less than or equal to the specified distance and the avoidance of the approach based on the detection result by the sensor 26.

With reference back to FIG. 1, the input interface 61 receives various types of instructions and information inputs from the operator. The input interface 61 is implemented by, for example, a trackball, a switch button, a mouse, a keyboard, a touch pad that performs an input operation by a touch on an operation surface, a touch screen having an integrated combination of a display screen and a touch pad, and a non-contact input circuit using an optical sensor, a voice input circuit, etc. The input interface 61 is connected to the processing circuit 60 to convert the input operation received from the operator into an electric signal and output the electric signal to the processing circuit 60. In this description, the input interface 61 is not limited to the one including a physical operating part such as a mouse and a keyboard. Examples of the input interface 61 include an electric signal processing circuit that receives an electric signal corresponding to an input operation from an external input device provided separately from the X-ray diagnostic apparatus 100 and outputs the electric signal to a control circuit.

The display 62 presents a graphical user interface (GUI) that receives input of an imaging condition, an X-ray image acquired by the processing circuit 60, and the like, under the control of the processing circuit 60. The display 62 is, for example, a display device such as a liquid crystal display. The display 62 is an example of a display unit. The display 62 may be provided outside the X-ray diagnostic apparatus 100.

The storage 63 stores programs corresponding to various functions read and executed by each circuit illustrated in FIG. 1. The storage 63 is implemented by, for example, a semiconductor memory device such as a random access memory (RAM) or a flash memory, a hard disk, or an optical disk. The storage 63 is an example of a storage unit.

The processing circuit 60 controls imaging processing by the X-ray diagnostic apparatus 100. For example, the processing circuit 60 reads an X-ray detection result from the X-ray detector 22 to acquire an X-ray image. The processing circuit 60 is an example of a control device according to the present embodiment.

More specifically, the processing circuit 60 according to the present embodiment includes an acquisition function 601, a determination function 602, a read function 603, a display control function 604, and a reception function 605. The acquisition function 601 is an example of an acquisition unit. The determination function 602 is an example of a determination unit. The read function 603 is an example of a read unit. The display control function 604 is an example of a display control unit. The reception function 605 is an example of the reception unit.

The acquisition function 601 acquires the setting information on the FOV, the SID, the rotation angle of the rotation mechanism 24, and the slide amount of the X-ray detector 22. For example, the acquisition function 601 acquires the setting information on the FOV based on an inspection order, or the like, received from an external device. The setting information on the FOV may be received from the operator by the reception function 605 described below. The acquisition function 601 acquires the SID, the rotation angle of the rotation mechanism 24, and the slide amount of the X-ray detector 22 from the movement-mechanism control circuit 51. Alternatively, the acquisition function 601 may acquire such information from the backward-and-forward movement unit 25, the rotation mechanism 24, and the slide mechanism 23.

The determination function 602 determines the reading range on the X-ray detector 22 or the clipping range of the X-ray detection result.

The reading range is a range on the X-ray detector 22 and is a range from which the read function 603 described below reads the detection result of the X-rays.

The clipping range is a region included in the detection result of the X-rays read by the X-ray detector 22 and acquired as an X-ray image.

Figure 9:
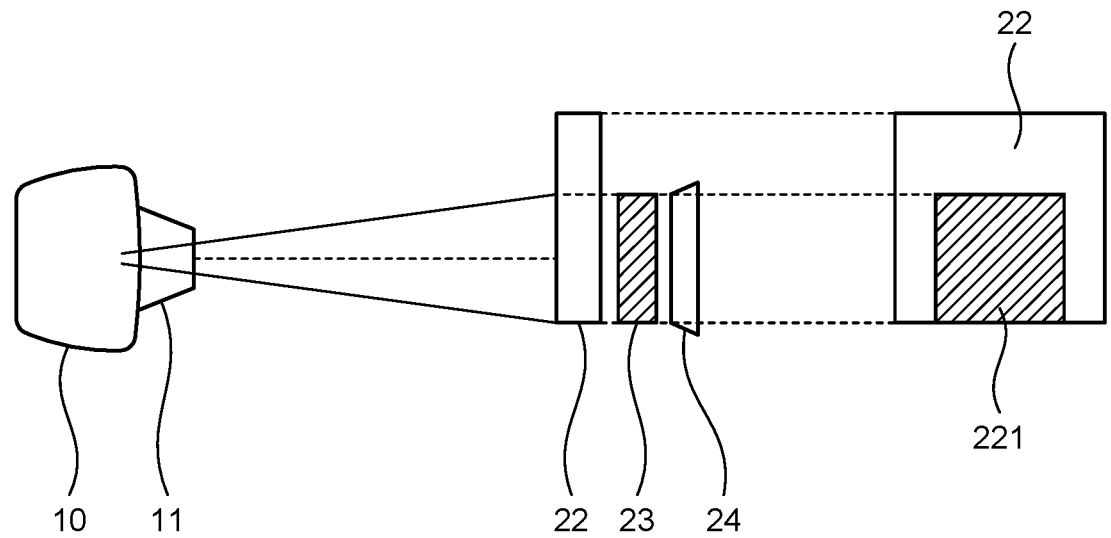
FIG. 9 is a diagram illustrating an example of a reading range according to the first embodiment.

FIG. 9 is a diagram illustrating an example of a reading range 221 according to the first embodiment. In the example illustrated in FIG. 9, the X-ray detector 22 is slid upward in FIG. 9 by the slide mechanism 23. Therefore, an upper portion of the X-ray detector 22 includes a region that falls outside the X-ray irradiation range. As the region outside the X-ray irradiation range is not needed for drawing the subject P, the determination function 602 determines the reading range 221 corresponding to the X-ray irradiation range.

Although the region corresponding to the X-ray irradiation range is set as the reading range 221 in FIG. 9, the determination function 602 may set, as a reading range, a region larger than the region corresponding to the X-ray irradiation range, for example, the entire surface of the X-ray detector 22. In this case, the determination function 602 may determine that only the region included in the reading range and corresponding to the X-ray irradiation range is a clipping range. For example, the region described as the reading range 221 in FIG. 9 may be a clipping range.

The determination function 602 determines the reading range or the clipping range based on, for example, the region corresponding to the FOV on the X-ray detector 22, the SID, the rotation angles of the slide mechanism 23 and the X-ray detector 22 by the rotation mechanism, and the slide amount of the X-ray detector 22 by the slide mechanism 23.

The specified range defined in accordance with the operation mode of the X-ray diagnostic apparatus 100 may be set as a reading range. For example, the determination function 602 may determine the FOV in accordance with the operation mode and set the region corresponding to the FOV on the X-ray detector 22 as a reading range. In this case, the determination function 602 may determine the clipping range within the specified reading range. The operation mode of the X-ray diagnostic apparatus 100 is provided for each type of inspection, for example.

The read function 603 reads the X-ray detection result from the reading range determined by the determination function 602 on the X-ray detector 22. More specifically, the read function 603 reads the X-ray detection result from the detection elements corresponding to the determined reading range among the plurality of detection elements included in the X-ray detector 22. When the clipping range has been determined by the determination function 602, the read function 603 deletes the data outside the clipping range from the read result.

The display control function 604 causes the display 62 to present the X-ray image based on the X-ray detection result read by the read function 603.

The reception function 605 receives various operations from the operator via the input interface 61. For example, the reception function 605 receives input of the FOV from the operator. The reception function 605 receives input from the operator to specify the operation mode. Receiving input from the operator may be referred to as "acquiring". In this case, both the acquisition function 601 and the reception function 605 may be an example of an acquisition unit.

In the X-ray diagnostic apparatus 100 illustrated in FIG. 1, as an example, each processing function is stored in the storage 63 in the form of a program executable by a computer. The movement-mechanism control circuit 51, the collimator control circuit 52, and the processing circuit 60 are processors that read and execute a program from the storage 63 to perform the function corresponding to each program. In other words, each circuit having read each program has the function corresponding to the read program.

For example, each of processing functions of the acquisition function 601, the determination function 602, the read function 603, the display control function 604, and the reception function 605, which are components of the processing circuit 60, is stored in the storage 63 in the form of a program executable by a computer. For example, the processing circuit 60 reads and executes a program from the storage 63 to perform the function corresponding to each program. In other words, the processing circuit 60 having read each program has each function illustrated in the processing circuit 60 of FIG. 1. In the description of FIG. 1, the single processor performs the processing functions performed by the acquisition function 601, the determination function 602, the read function 603, the display control function 604, and the reception function 605; however, independent processors may be combined to form the processing circuit 60, and each of the processors may execute a program to perform a function. Although the storage 63 is illustrated in FIG. 1, a plurality of storage may be provided.

Although the movement-mechanism control circuit 51, the collimator control circuit 52, and the processing circuit 60 are separately illustrated in FIG. 1, these functions may be performed by a single processor. In FIG. 1, the movement-mechanism control circuit 51 controls the slide mechanism 23, the rotation mechanism 24, the backward-and-forward movement unit 25, the C-arm rotation/movement mechanism 53, and the top-plate movement mechanism 54; however, the slide mechanism 23, the rotation mechanism 24, the backward-and-forward movement unit 25, the C-arm rotation/movement mechanism 53, and the top-plate movement mechanism 54 may individually include a processing circuit. For example, the function described as the processing of the movement-mechanism control circuit 51 may be executed by the slide mechanism 23, the rotation mechanism 24, the backward-and-forward movement unit 25, the C-arm rotation/movement mechanism 53, or the top-plate movement mechanism 54.

In the above description, for example, the "processor" reads and executes the program corresponding to each function from the storage, but the embodiment is not limited thereto. The term "processor" is, for example, a central processing unit (CPU), a graphics processing unit (GPU), or a circuit such as an application specific integrated circuit (ASIC) or a programmable logic device (e.g., a simple programmable logic device (SPLD), a complex programmable logic device (CPLD), and a field programmable gate array (FPGA)). When the processor is, for example, a CPU, the processor reads and executes a program stored in the storage to perform a function. On the other hand, when the processor is an ASIC, the function is directly installed as a logic circuit in a circuit of the processor instead of storing the program in the storage 63. With regard to each processor according to the present embodiment, each processor is not always configured as a single circuit, but may be configured as a single processor by combining a plurality of independent circuits to perform its function. A plurality of components in FIG. 1 may be integrated into one processor to perform its function.

Next, the flow of the slide and rotation operation executed by the X-ray diagnostic apparatus 100 according to the present embodiment configured as described above is described.

Figure 10:
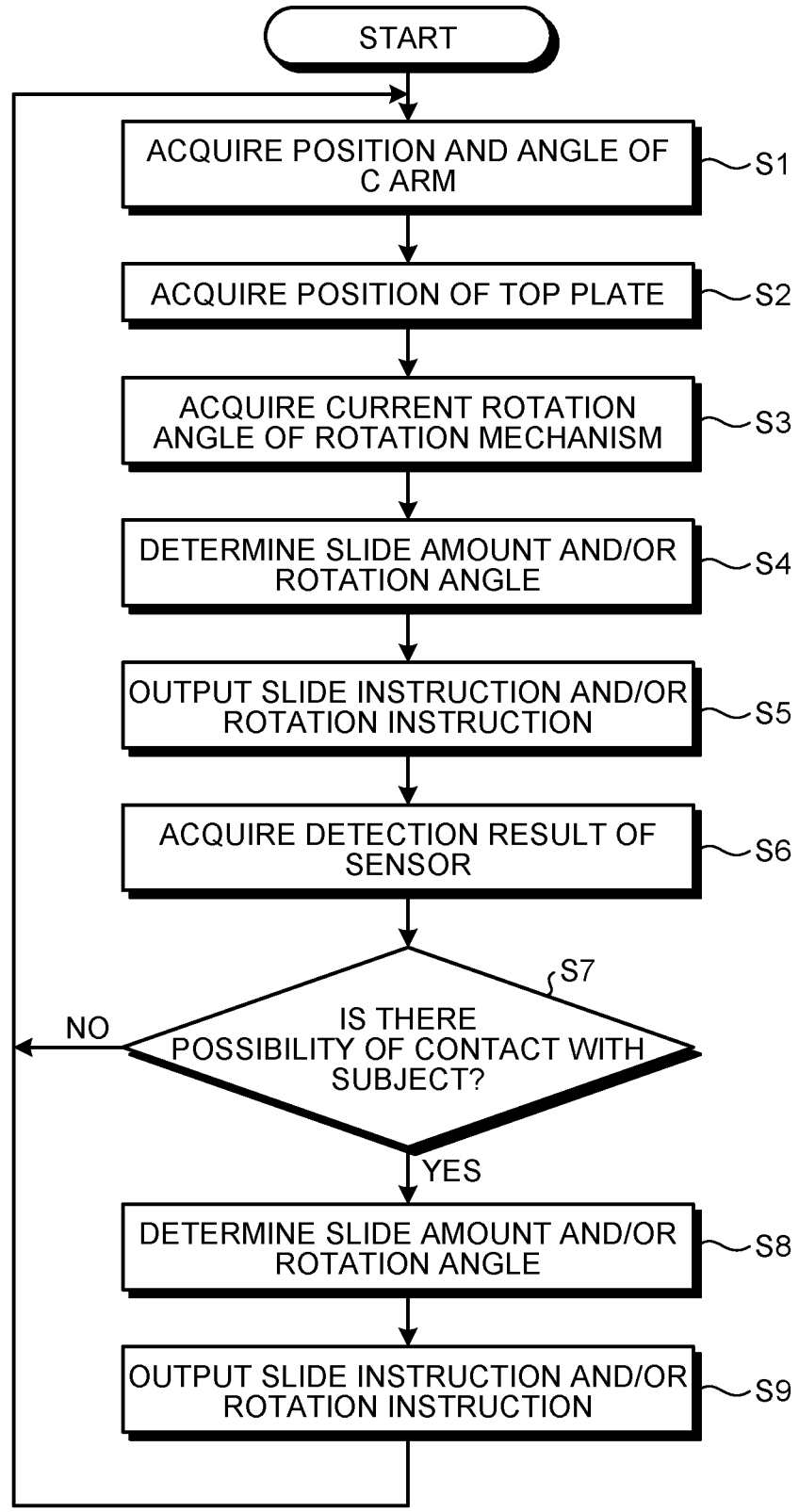
FIG. 10 is a flowchart illustrating an example of a flow of a slide and rotation operation according to the first embodiment.

FIG. 10 is a flowchart illustrating an example of the flow of the slide and rotation operation according to the first embodiment.

First, the movement-mechanism control circuit 51 acquires the current position and angle of the C arm 40 from the C-arm rotation/movement mechanism 53 (S1).

The movement-mechanism control circuit 51 acquires the current position of the top plate 30 from the top-plate movement mechanism 54 (S2).

The movement-mechanism control circuit 51 acquires the current rotation angle of the rotation mechanism 24 from the rotation mechanism 24 (S3).

The movement-mechanism control circuit 51 determines the slide amount of the X-ray detector 22 and/or the rotation angle of the rotation mechanism 24. More specifically, the movement-mechanism control circuit 51 determines the slide amount of the X-ray detector 22 based on the acquired position and angle of the C arm 40 and the position of the top plate 30. For example, the movement-mechanism control circuit 51 calculates the clinical angle based on the angle of the C arm 40 and the position of the top plate 30 and determines the slide amount of the X-ray detector 22 based on the clinical angle. The movement-mechanism control circuit 51 specifies the current slide axis direction of the slide mechanism 23 based on the acquired current rotation angle of the rotation mechanism 24 and determines the rotation angle of the rotation mechanism 24 such that the direction in which the X-ray detector 22 is to slide matches the slide axis direction of the slide mechanism 23 (S4).

As described above, the movement-mechanism control circuit 51 may further determine the slide amount based on the FOV. When it is determined that the direction in which the X-ray detector 22 is to slide matches the slide axis direction of the slide mechanism 23, the movement-mechanism control circuit 51 does not need to determine the rotation angle in particular.

Then, the movement-mechanism control circuit 51 outputs a slide instruction and a rotation instruction to the slide mechanism 23 and the rotation mechanism 24 based on the determined slide amount and rotation angle. When it is determined that either slide or rotation is needed, the movement-mechanism control circuit 51 outputs a slide instruction or a rotation instruction to the slide mechanism 23 or the rotation mechanism 24 (S5).

At S4 to S5, the processing flow is described based on the assumption that the X-ray detector 22 needs to be slid, but the movement-mechanism control circuit 51 does not give a slide instruction when it is determined that the X-ray detector 22 does not need to be slid based on the acquired position and angle of the C arm 40 and the position of the top plate 30.

The movement-mechanism control circuit 51 acquires the detection result regarding the approach between the X-ray detector 22 and the subject P from the sensor 26 (S6).

The movement-mechanism control circuit 51 determines whether there is a possibility of the contact between the X-ray detector 22 and the subject P based on the detection result of the sensor 26 (S7).

For example, the movement-mechanism control circuit 51 determines that there is a possibility of the contact between the X-ray detector 22 and the subject P when the distance between the X-ray detector 22 and the subject P is less than or equal to the specified distance ("Yes" at S7). The movement-mechanism control circuit 51 determines that there is no possibility of the contact between the X-ray detector 22 and the subject P when the distance between the X-ray detector 22 and the subject P is more than the specified distance ("No" at S7). The movement-mechanism control circuit 51 returns to the process at S1 when it is determined that there is no possibility of the contact between the X-ray detector 22 and the subject P.

When it is determined that there is a possibility of the contact between the X-ray detector 22 and the subject P, the movement-mechanism control circuit 51 determines the slide amount and the rotation angle to move the X-ray detector 22 in the direction away from the subject P (S8).

When the contact may be avoided by either slide or rotation, the movement-mechanism control circuit 51 may determine either the slide amount or the rotation angle.

When the sensor 26 detects the contact between the X-ray detector 22 and the subject P, the movement-mechanism control circuit 51 may proceed to the process at S8.

Then, the movement-mechanism control circuit 51 outputs a slide instruction and a rotation instruction to the slide mechanism 23 and the rotation mechanism 24 based on the determined slide amount and rotation angle. When either the slide amount or the rotation angle is determined, the movement-mechanism control circuit 51 outputs the slide instruction or the rotation instruction to the slide mechanism 23 or the rotation mechanism 24 (S9). Then, the process at S1 is returned, and the process of this flowchart is repeated while the X-ray diagnostic apparatus 100 is in operation.

Next, the flow of a reading-range determination process executed by the X-ray diagnostic apparatus 100 configured as described above according to the present embodiment is described.

Figure 11:
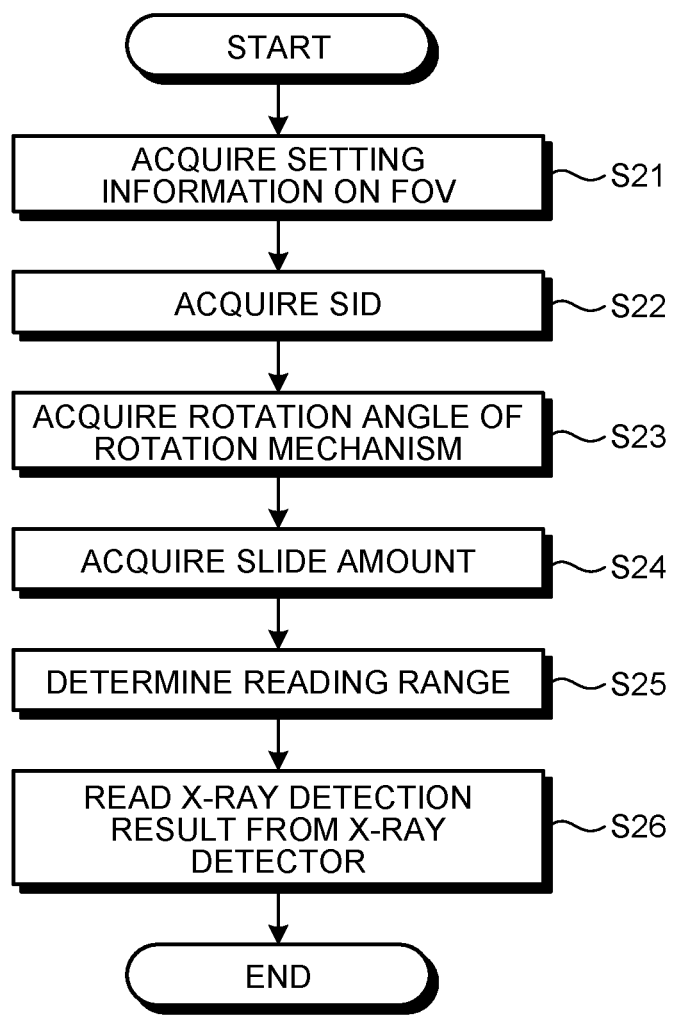
FIG. 11 is a flowchart illustrating an example of a flow of a process to determine the reading range according to the first embodiment.

FIG. 11 is a flowchart illustrating an example of the flow of the process to determine the reading range 221 according to the first embodiment. The process of this flowchart is based on the assumption that the X-ray tube 10 has emitted X-rays.

First, the acquisition function 601 of the processing circuit 60 acquires the setting information on the FOV (S21).

The acquisition function 601 acquires the current SID from the movement-mechanism control circuit 51 (S22).

The acquisition function 601 acquires the current rotation angle of the rotation mechanism 24 from the movement-mechanism control circuit 51 (S23).

The acquisition function 601 acquires the current slide amount from the movement-mechanism control circuit 51 (S24).

The determination function 602 determines the reading range 221 based on the FOV, the SID, the current rotation angle, and the current slide amount, acquired by the acquisition function 601 (S25).

The read function 603 reads the X-ray detection result from the detection elements corresponding to the reading range 221 determined by the determination function 602 on the X-ray detector 22 (S26). Here, the process of this flowchart ends.

Although the process to determine the reading range 221 is described as an example in FIG. 11, the determination function 602 may determine both the reading range 221 and the clipping range or may determine only the clipping range.

As described above, the X-ray diagnostic apparatus 100 according to the present embodiment includes the X-ray detector 22, the grid 21 that has a fixed relative position to the X-ray detector 22 and is provided with stripes extending in the first direction, the slide mechanism 23 that holds the X-ray detector 22 so as to slide in the first direction, the rotation mechanism 24 that rotatably holds the slide mechanism 23, and the C arm 40 that holds the rotation mechanism 24 and is operable. Therefore, the X-ray diagnostic apparatus 100 according to the present embodiment may improve the flexibility in the positions of the X-ray detector 22 and the C arm 40 during imaging while maintaining the scattered ray removal function of the grid 21.

Conventionally, in the case of, for example, a relatively large X-ray detector having a size of 12 inches or more per side and capable of imaging in a wide range, there may be a low flexibility in the positions of the X-ray detector and the C arm during imaging, as compared with a small X-ray detector having a size of 8 inches per side. Furthermore, as a small X-ray detector has a limited range in which imaging is possible at one time, the small X-ray detector may be unsuitable for catheter treatment, or the like, for a structural heart disease (SHD) that requires a wide field of view.

On the other hand, the X-ray diagnostic apparatus 100 according to the present embodiment may improve the flexibility in the positions of the X-ray detector 22 and the C arm 40 during imaging, and therefore the large X-ray detector 22 may be used in a situation where the conventional small X-ray detection has been used. Thus, it is possible to achieve both the wide field of view and the flexibility in the positions of the X-ray detector 22 and the C arm 40 during imaging.

In the X-ray diagnostic apparatus 100 according to the present embodiment, as the arrangement direction of the grid 21 is identical to the sliding direction of the X-ray detector 22, the X-ray irradiation angle with respect to the stripe on the grid 21 does not change even though the grid 21 and the X-ray detector 22 are slid, and thus the function to remove scattered ray components may be maintained.

In the X-ray diagnostic apparatus 100 according to the present embodiment, the slide mechanism 23 controls the slide amount of the X-ray detector 22 based on the angle of the C arm 40. Thus, with the X-ray diagnostic apparatus 100 according to the present embodiment, when the C arm 40 is moved or rotated for imaging, the X-ray detector 22 may be moved to an appropriate position in accordance with the position after a movement.

In the X-ray diagnostic apparatus 100 according to the present embodiment, the slide mechanism 23 controls the slide amount of the X-ray detector 22 based on the FOV and the angle of the C arm 40. Thus, with the X-ray diagnostic apparatus 100 according to the present embodiment, the X-ray detector 22 may be moved as appropriate in accordance with the position to be taken by the X-ray detector 22 for imaging with the subject P.

In the X-ray diagnostic apparatus 100 according to the present embodiment, the slide mechanism 23 controls the slide amount of the X-ray detector 22 based on the angle of the C arm 40 and the position of the top plate 30. Therefore, with the X-ray diagnostic apparatus 100 according to the present embodiment, the slide amount of the X-ray detector 22 may be determined in accordance with the relative position between the C arm 40 and the top plate 30, and thus the possibility of the contact between the subject P and the X-ray detector 22 may be reduced.

In the X-ray diagnostic apparatus 100 according to the present embodiment, the slide mechanism 23 controls the slide amount of the X-ray detector 22 based on the clinical angle calculated based on the angle of the C arm 40 and the position of the top plate 30. Therefore, with the X-ray diagnostic apparatus 100 according to the present embodiment, the possibility of the contact between the subject P and the X-ray detector 22 may be further reduced with higher accuracy.

In the X-ray diagnostic apparatus 100 according to the present embodiment, the rotation mechanism 24 rotates the slide mechanism 23 based on the operating direction of the C arm 40 and the position of the top plate 30 such that the first direction becomes parallel to the direction in which the X-ray detector 22 moves away from the subject P. Thus, the X-ray diagnostic apparatus 100 according to the present embodiment makes it possible to retract the X-ray detector 22 in various directions and to handle various positional relationships between the X-ray detector 22 and the subject P.

In the X-ray diagnostic apparatus 100 according to the present embodiment, the slide mechanism 23 further controls the slide amount of the X-ray detector 22 based on the region corresponding to the FOV on the X-ray detector 22. Therefore, with the X-ray diagnostic apparatus 100 according to the present embodiment, the X-ray detector 22 may be slid within an appropriate range so that the irradiation range of the X-rays does not fall outside the X-ray detector 22.

The X-ray diagnostic apparatus 100 according to the present embodiment further includes the sensor 26, and when the sensor 26 detects the approach between the X-ray detector 22 and the subject P, the X-ray detector 22 is slid in the direction away from the subject P along the first direction. Therefore, with the X-ray diagnostic apparatus 100 according to the present embodiment, for example, even when the subject P is moved toward the X-ray detector 22, the approach more than necessary between the X-ray detector 22 and the subject P may be reduced.

The slide mechanism 23 slides the X-ray detector 22 based on the detection result of the approach between the X-ray detector 22 and the subject P by the sensor 26 and the region corresponding to the FOV on the X-ray detector 22. Therefore, with the X-ray diagnostic apparatus 100 according to the present embodiment, an appropriate slide amount may be determined such that the entire irradiation range of the X-rays corresponding to the FOV is included in the X-ray detector 22 while the approach more than necessary between the X-ray detector 22 and the subject P is reduced.

In the X-ray diagnostic apparatus 100 according to the present embodiment, the reading range on the X-ray detector 22 or the clipping range of the X-ray detection result is determined based on the region corresponding to the FOV on the X-ray detector 22, the SID, the rotation angles of the slide mechanism 23 and the X-ray detector 22 by the rotation mechanism 24, and the slide amount of the X-ray detector 22 by the slide mechanism 23. Therefore, with the X-ray diagnostic apparatus 100 according to the present embodiment, the data for acquiring the X-ray image may be efficiently acquired in accordance with the region corresponding to the FOV on the slid X-ray detector 22.

According to the present embodiment, the movement-mechanism control circuit 51 determines the slide amount of the X-ray detector 22 based on the clinical angle calculated based on the angle of the C arm 40 and the position of the top plate 30; however, a configuration may be such that the slide amount is determined simply based on the angle of the C arm 40 or may be determined based on the angle of the C arm 40 and the position of the top plate 30 instead of the clinical angle.

Second Embodiment

According to the first embodiment described above, the slide mechanism 23 slides the X-ray detector 22 to prevent the distance between the X-ray detector 22 and the subject P from being less than or equal to the specified distance. According to a second embodiment, the backward-and-forward movement unit 25 further increases the SID to secure the distance between the X-ray detector 22 and the subject P.

The X-ray diagnostic apparatus 100 according to the present embodiment has the same configuration as that in the first embodiment described with reference to FIG. 1.

The backward-and-forward movement unit 25 according to the present embodiment operates the X-ray detector 22 in a direction away from the subject P when the slide mechanism 23 has slid the X-ray detector 22 from the initial position and the sensor 26 has detected the approach between the X-ray detector 22 and the subject P.

For example, the backward-and-forward movement unit 25 may operate the X-ray detector 22 in a direction away from the subject P only when the slide mechanism 23 has moved the X-ray detector 22 to the upper limit of the slide distance and the sensor 26 has detected the approach between the X-ray detector 22 and the subject P.

When the backward-and-forward movement unit 25 operates the X-ray detector 22 in a direction away from the subject P, the slide mechanism 23 according to the present embodiment slides the X-ray detector 22 in accordance with the irradiation range of the X-rays of the X-ray tube 10. This is because the region corresponding to the FOV on the X-ray detector 22 changes due to the movement of the X-ray detector 22 by the backward-and-forward movement unit 25 in a direction in which the SID increases. By sliding the X-ray detector 22, the slide mechanism 23 moves the X-ray detector 22 in a direction close to the subject P such that the irradiation range of the X-rays after the change in the SID falls within the detection surface of the X-ray detector 22. The slide mechanism 23 slides the X-ray detector 22 as long as the distance between the X-ray detector 22 and the subject P does not become less than or equal to the specified distance.

As described above, with the X-ray diagnostic apparatus 100 according to the present embodiment, the backward-and-forward movement unit 25 may further reduce the approach more than necessary between the X-ray detector 22 and the subject P, and thus the flexibility in the positions of the X-ray detector 22 and the C arm 40 during imaging may be further improved while the advantageous effect of the first embodiment is provided.

Third Embodiment

In the case described according to the first embodiment described above, the X-ray diagnostic apparatus 100 has a single-plane configuration including the single C arm 40, but the X-ray diagnostic apparatus 100 may have a biplane configuration.

For example, the X-ray diagnostic apparatus 100 according to the present embodiment further includes an Ω arm in addition to the C arm 40. The C arm 40 is an example of a first arm according to the present embodiment. The Ω arm is an example of a second arm according to the present embodiment.

The C arm 40 is used, for example, to primarily capture the front surface of the subject P. The Ω arm is used to primarily capture a side surface of the subject P.

The C arm 40 holds the X-ray tube 10, the X-ray collimator 11, the grid 21, the X-ray detector 22, the slide mechanism 23, the rotation mechanism 24, the backward-and-forward movement unit 25, and the sensor 26, as in the first embodiment. According to the present embodiment, the X-ray tube 10 included in the C arm 40 is an example of a first X-ray tube. The X-ray detector 22 included in the C arm 40 is an example of a first X-ray detector. The grid 21 included in the C arm 40 is an example of a first grid. The slide mechanism 23 included in the C arm 40 is an example of a first slide mechanism. The rotation mechanism 24 included in the C arm 40 is an example of a first rotation mechanism.

In the same manner as the C arm 40, the Ω arm holds an X-ray tube, an X-ray collimator, a grid, an X-ray detector, a slide mechanism, a rotation mechanism, a backward-and-forward movement unit, and a sensor. According to the present embodiment, the X-ray tube included in the Ω arm is an example of a second X-ray tube. The X-ray detector included in the Ω arm is an example of a second X-ray detector. The grid included in the Ω arm is an example of a second grid. The slide mechanism included in the Ω arm is an example of a second slide mechanism. The rotation mechanism included in the Ω arm is an example of a second rotation mechanism.

When the X-ray detector 22 of the C arm 40 is located on a path of X-rays emitted from the X-ray tube of the Ω arm to the X-ray detector of the Ω arm, the slide mechanism 23 of the C arm 40 slides the X-ray detector 22 of the C arm 40 such that the X-ray detector 22 of the C arm 40 falls outside the path. The slide mechanism of the Ω arm also has the same function.

As described above, with the X-ray diagnostic apparatus 100 according to the present embodiment, the same advantageous effect as that in the first embodiment may be provided even in the case of biplane, and it is possible to reduce the entry of the X-ray detector of one of the arms into an X-ray irradiation path of the other arm.

Fourth Embodiment

According to a fourth embodiment, the X-ray detector 22 is further slid to improve the resolution of an X-ray image.

The X-ray diagnostic apparatus 100 according to the present embodiment has the same configuration as that in the first embodiment described with reference to FIG. 1.

Figure 12:
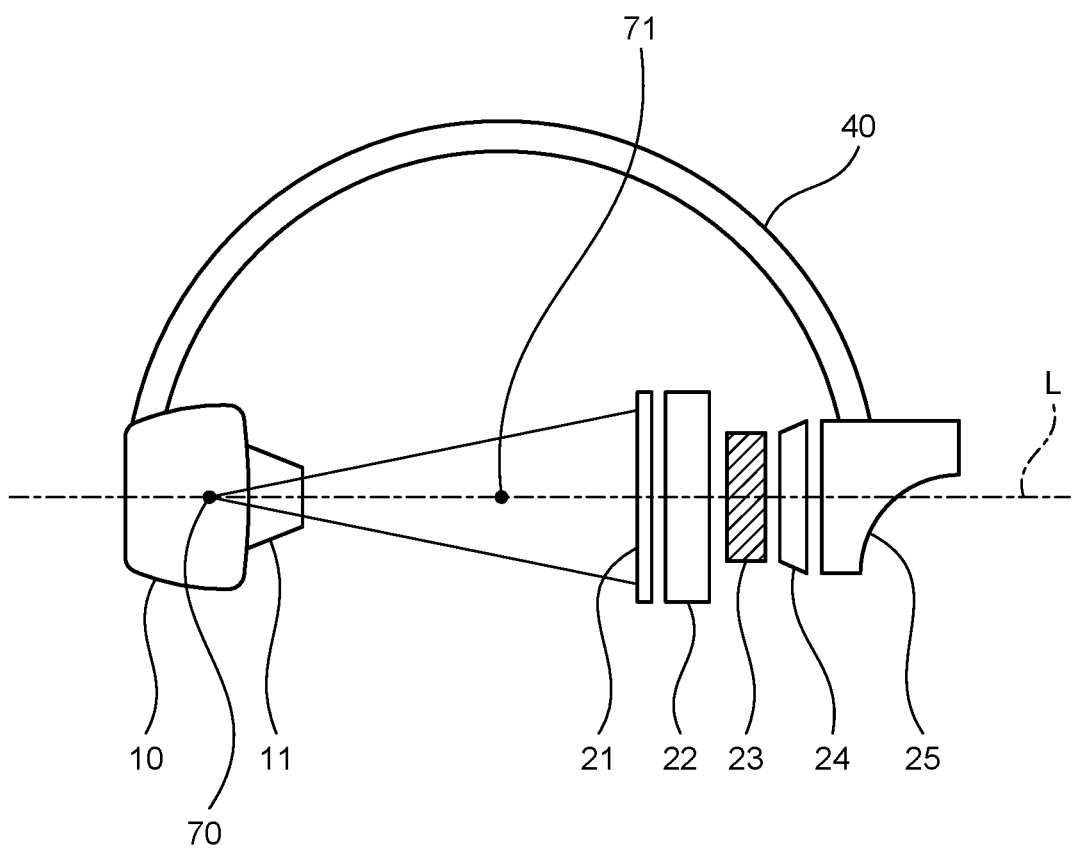
FIG. 12 is a diagram illustrating an example of a positional relationship among a general focal point, an isocenter, and the X-ray detector.

FIG. 12 is a diagram illustrating an example of the positional relationship among a general focal point 70, an iso-center 71, and the X-ray detector 22. The focal point 70 is the focal point of X-rays emitted from the X-ray tube 10 and focused by the X-ray collimator 11.

As illustrated in FIG. 12, the centers of the focal point 70, the iso-center 71, and the X-ray detector 22 are typically arranged so as to be located on a straight line. In FIG. 12, it is assumed that the X-ray detector 22 is located at the initial position before being slid by the slide mechanism 23. In this case, the focal point 70, the iso-center 71, and the X-ray detector 22 are arranged on the straight line L.

Here, in the X-ray tube 10, the inclination angle of the anode defines the maximum irradiation angle. Typically, when the focal point 70 is viewed from the side of the X-ray detector 22, the size of the focal point 70 appears to be small when viewed from the anode side as compared to that when viewed from the side close to the cathode. The smaller the focal point 70 appears to be, the higher the resolution of the X-ray image. Therefore, the resolution of the X-ray image captured by the X-ray detector 22 is higher on the anode side than on the cathode side.

As the size of the X-ray detector 22 is larger, the maximum irradiation angle needed is larger, and therefore the inclination angle of the anode of the X-ray tube 10 is larger. Therefore, when the area of the focal point on the anode surface is identical, the apparent size of the focal point when viewed on the line connecting the focal point 70 and the iso-center is also larger. That is, a large X-ray detector has a low resolution at the same FOV as compared to a small X-ray detector.

Therefore, according to the present embodiment, the X-ray collimator 11 narrows X-rays such that the X-rays on the side of the anode with respect to the middle between the cathode and the anode of the X-ray tube 10 are larger in number than the X-rays on the side of the cathode with respect to the middle.

Figure 13:
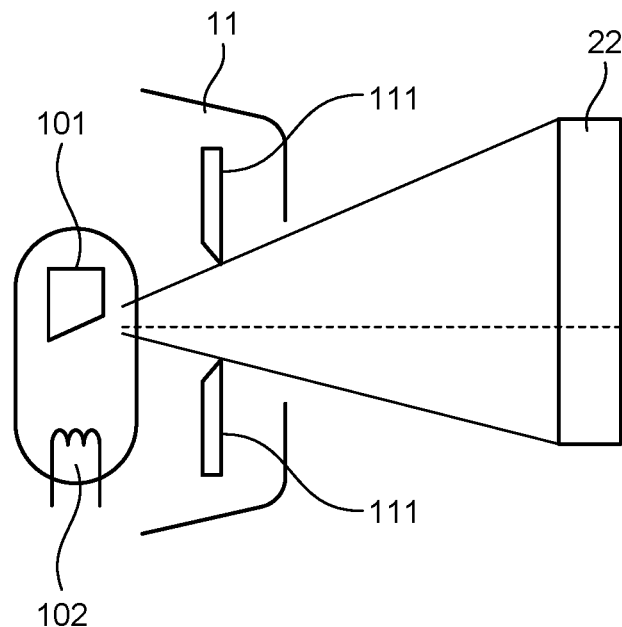
FIG. 13 is a diagram illustrating an example of details of an X-ray tube and an X-ray collimator according to a fourth embodiment.

FIG. 13 is a diagram illustrating an example of details of the X-ray tube 10 and the X-ray collimator 11 according to the fourth embodiment. As illustrated in FIG. 13, the X-ray tube 10 includes a cathode 102 that generates thermoelectrons and an anode 101 that generates X-rays upon collision of thermoelectrons. The X-ray collimator 11 includes a plurality of collimator blades 111.

The X-ray image acquirable by the detection surface of the X-ray detector 22 has a lower resolution on the side of the cathode 102, i.e., on a lower side in FIG. 13. The X-ray image has an improved resolution on the side of the anode 101, i.e., on an upper side in FIG. 13.

Therefore, according to the present embodiment, when the FOV is changed, the X-ray collimator 11 moves the collimator blades 111 to narrow the irradiation range to the side of the anode 101 with respect to the middle between the cathode 102 and the anode 101. In the example illustrated in FIG. 13, too, the X-ray collimator 11 causes a larger number of X-rays generated from the X-ray tube 10 to be emitted to the X-ray detector 22 on the side of the anode 101 with respect to the middle than on the side of the cathode 102 with respect to the middle.

Although the slide mechanism 23 and the grid 21 are not illustrated in FIG. 13, the slide mechanism 23, the X-ray detector 22, and the grid 21 are arranged such that the first direction of the grid 21 is parallel to the direction connecting the cathode and the anode of the X-ray tube 10. That is, the slide mechanism 23 according to the present embodiment may slide the X-ray detector 22 in parallel with the direction connecting the cathode and the anode of the X-ray tube 10.

Figure 14:
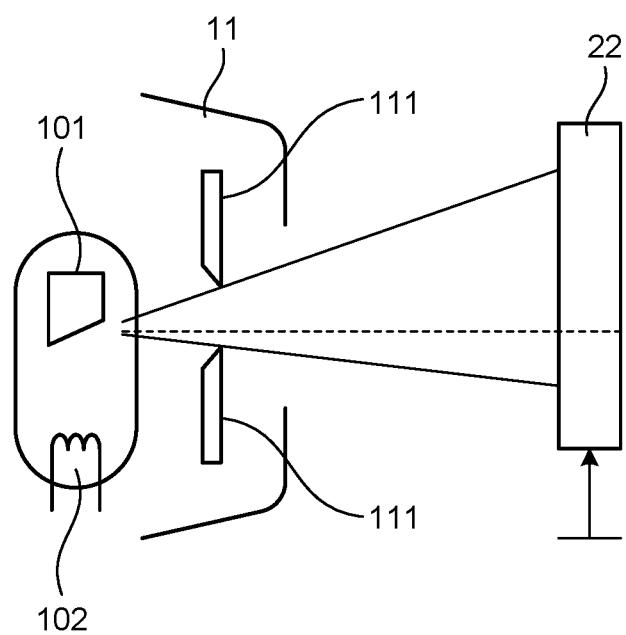
FIG. 14 is a diagram illustrating an example of a state where an irradiation range of X-rays is narrower than that in FIG. 13.

FIG. 14 is a diagram illustrating an example of a state where the irradiation range of the X-rays is narrower than that in FIG. 13. When the irradiation range is narrowed, the X-ray irradiated region on the X-ray detector 22 becomes narrower. Therefore, the X-ray irradiated region on the X-ray detector 22 may deviate from the center of the X-ray detector 22.

Therefore, the slide mechanism 23 according to the present embodiment slides the center of the X-ray detector 22 to the center of the irradiation range of the X-rays. In other words, the slide mechanism 23 slides the X-ray detector 22 to the side of the anode 101 in accordance with the irradiation range of the X-rays narrowed by the X-ray collimator 11.

For example, typically, the X-ray detector 22 may have the upper limit of the reading frame rate depending on the size of X-ray image data to be read. There is also the X-ray detector 22 that may clip and read only at the center in accordance with the specification. The slide mechanism 23 in the X-ray diagnostic apparatus 100 according to the present embodiment slides the center of the X-ray detector 22 to the center of the irradiation range of the X-rays so that, even when the X-ray collimator 11 narrows the irradiation range of the X-rays unevenly to the side of the anode 101, the X-rays are detectable at the central portion of the X-ray detector 22.

Therefore, with the X-ray diagnostic apparatus 100 according to the present embodiment, a reduction in the resolution due to an increase in the size of the X-ray detector 22 may be further reduced while the advantageous effect of the first embodiment is provided.

The position of the iso-center 71 shifts due to the sliding of the X-ray detector 22. Accordingly, particularly, the rotation of the C arm 40 in the slide rotation direction is not about the iso-center 71. Therefore, the X-ray collimator 11 and the slide mechanism 23 may perform the above-described control to narrow the irradiation range to the side of the anode 101 with respect to the middle between the cathode 102 and the anode 101 only when the slide range of the C arm 40 has a specified value. When the slide range of the C arm 40 has an angle other than the specified value, the control may be performed to uniformly narrow the irradiation range to the side of the cathode 102 and the side of the anode 101 as in a conventional technique. It is also possible to continuously switch the control for narrowing the irradiation range to the anode 101 and the control for narrowing the irradiation range of X-rays around the focal point 70.

Various types of data processed in this description are typically digital data.

According to at least one of the embodiments described above, the flexibility in the positions of the X-ray detector and the arm during imaging may be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
an X-ray tube configured to emit X-rays;
an X-ray detector configured to detect the X-rays emitted from the X-ray tube;
a grid configured to have a fixed relative position to the X-ray detector and being provided with stripes extending in a first direction to remove scattered rays;
a slide mechanism including at least one slide rail along the first direction and configured to hold the X-ray detector so as to slide the X-ray detector in the first direction;
a rotary mechanism including a rotation shaft and configured to rotatably hold the slide mechanism;
an arm configured to hold the rotary mechanism, and being operable,
a top plate on which a subject is placed; and
a top-plate movement mechanism configured to move and tilt the top plate, wherein
the slide mechanism is further configured to control a slide amount of the X-ray detector based on a clinical angle calculated based on an angle of the arm and a position of the top plate, and
the rotary mechanism is further configured to rotate the slide mechanism based on an operating direction of the arm and the position of the top plate such that the first direction becomes parallel to a direction in which the X-ray detector moves away from the subject.

2. The X-ray diagnostic apparatus according to claim 1, wherein the slide mechanism is further configured to control the slide amount of the X-ray detector based on an imaging field of view.

3. The X-ray diagnostic apparatus according to claim 1, wherein the slide mechanism is further configured to control the slide amount of the X-ray detector based on a region corresponding to an imaging field of view on the X-ray detector.

4. The X-ray diagnostic apparatus according to claim 1, further comprising a detector configured to, when the X-ray detector and the subject approach each other by a specified distance or less, detect the approach, wherein when the detector detects the approach between the X-ray detector and the subject, the slide mechanism is further configured to slide the X-ray detector in a direction away from the subject along the first direction.

5. The X-ray diagnostic apparatus according to claim 1, further comprising a control device configured to read a detection result of the X-rays from the X-ray detector to acquire an X-ray image, wherein
the control device is further configured to determine a reading range on the X-ray detector or a clipping range of the detection result of the X-rays based on a region corresponding to an imaging field of view on the X-ray detector, a source-to-image receptor distance, which is a distance between the X-ray tube and the X-ray detector, rotation angles of the slide mechanism and the X-ray detector by the rotary mechanism, and a slide amount of the X-ray detector by the slide mechanism,
the reading range is a range on the X-ray detector and is a range from which the control device reads the detection result of the X-rays, and
the clipping range is a region included in the detection result of the X-rays read by the X-ray detector and acquired as the X-ray image by the control device.

6. The X-ray diagnostic apparatus according to claim 1, wherein the slide mechanism, the X-ray detector, and the grid are arranged such that the first direction of the grid is parallel to a direction connecting a cathode and an anode of the X-ray tube.

7. The X-ray diagnostic apparatus according to claim 4, wherein the slide mechanism is further configured to slide the X-ray detector based on a detection result of the approach between the X-ray detector and the subject by the detector and a region corresponding to an imaging field of view on the X-ray detector.

8. The X-ray diagnostic apparatus according to claim 6, further comprising an X-ray collimator that narrows the X-rays emitted from the X-ray tube, wherein
the X-ray collimator narrows the X-rays such that the X-rays emitted on a side of the anode with respect to a middle between the cathode and the anode of the X-ray tube are larger in number than the X-rays on a side of the cathode with respect to the middle.

9. The X-ray diagnostic apparatus according to claim 8, wherein the slide mechanism is further configured to slide the X-ray detector to the side of the anode in accordance with an irradiation range of the X-rays narrowed by the X-ray collimator.

10. An X-ray diagnostic apparatus, comprising:
an X-ray tube configured to emit X-rays;
an X-ray detector configured to detect the X-rays emitted from the X-ray tube;
a grid configured to have a fixed relative position to the X-ray detector and being provided with stripes extending in a first direction to remove scattered rays;
a slide mechanism including at least one slide rail along the first direction and configured to hold the X-ray detector so as to slide the X-ray detector in the first direction;
a rotary mechanism including a rotation shaft and configured to rotatably hold the slide mechanism;
an arm configured to hold the rotary mechanism, and being operable;
a detector configured to, when the X-ray detector and a subject approach each other by a specified distance or less, detect the approach; and a backward-and-forward movement mechanism configured to adjust a source-to-image receptor distance, which is a distance between the X-ray tube and the X-ray detector, wherein the backward-and-forward movement mechanism is further configured to operate the X-ray detector in a direction away from the subject when the slide mechanism has slid the X-ray detector from an initial position and the detector detects the approach between the X-ray detector and the subject, when the detector detects the approach between the X-ray detector and the subject, the slide mechanism is further configured to slide the X-ray detector in a direction away from the subject along the first direction, and when the backward-and-forward movement mechanism has operated the X-ray detector in the direction away from the subject, the slide mechanism is further configured to slide the X-ray detector in accordance with an irradiation range of the X-rays from the X-ray tube.

\* \* \* \* \*